US00RE39325E

(19) United States
(12) Reissued Patent
Bryan

(10) Patent Number: US RE39,325 E
(45) Date of Reissued Patent: Oct. 3, 2006

(54) SPINAL FIXATION APPARATUS AND METHOD

(76) Inventor: Donald W. Bryan, 6151 S. Woodland Dr., Ogden, UT (US) 84403

(21) Appl. No.: 09/948,870

(22) Filed: Sep. 7, 2001

Related U.S. Patent Documents

Reissue of:
(64) Patent No.: 5,947,965
Issued: Sep. 7, 1999
Appl. No.: 08/707,991
Filed: Mar. 11, 1996

U.S. Applications:
(63) Continuation-in-part of application No. 08/232,371, filed on Apr. 25, 1994, now Pat. No. 5,498,262, which is a continuation-in-part of application No. 07/999,005, filed on Dec. 31, 1992, now Pat. No. 5,306,275.

(51) Int. Cl.
*A61B 17/70* (2006.01)

(52) U.S. Cl. ..... 606/61; 606/69; 606/73
(58) Field of Classification Search ..... 606/60, 606/61, 72, 73, 53, 54, 59; 623/17.11
See application file for complete search history.

(56) References Cited

U.S. PATENT DOCUMENTS

| | | | | | |
|---|---|---|---|---|---|
| 4,887,595 | A | * | 12/1989 | Heinig et al. | 606/61 |
| 4,920,959 | A | | 5/1990 | Witzel et al. | |
| 4,998,936 | A | * | 3/1991 | Mehdian | 606/61 |
| 5,030,220 | A | | 7/1991 | Howland | |
| 5,122,131 | A | | 6/1992 | Tsou | |
| 5,129,900 | A | * | 7/1992 | Asher et al. | 606/61 |
| 5,154,719 | A | | 10/1992 | Cotrel | |
| 5,171,279 | A | | 12/1992 | Mathews | |
| 5,190,543 | A | | 3/1993 | Schläpfer | |
| 5,217,497 | A | | 6/1993 | Mehdian | |
| 5,219,349 | A | | 6/1993 | Krag et al. | |
| 5,242,445 | A | | 9/1993 | Ashman | |
| 5,261,907 | A | | 11/1993 | Vignaud et al. | |
| 5,282,862 | A | * | 2/1994 | Baker et al. | 623/17 |
| 5,344,422 | A | * | 9/1994 | Frigg | 606/61 |
| 5,352,225 | A | | 10/1994 | Yuan et al. | |
| 5,360,429 | A | | 11/1994 | Jeanson et al. | |
| 5,380,325 | A | * | 1/1995 | Lahille et al. | 606/61 |
| 5,437,669 | A | * | 8/1995 | Yuan et al. | 606/61 |
| 5,498,262 | A | * | 3/1996 | Bryan | 606/61 |
| 5,674,221 | A | * | 10/1997 | Hein et al. | 606/54 |
| 5,676,665 | A | * | 10/1997 | Bryan | 606/61 |
| 5,716,355 | A | * | 2/1998 | Jackson et al. | 606/61 |

FOREIGN PATENT DOCUMENTS

| | | |
|---|---|---|
| EP | 0 553 424 A1 | 8/1993 |

* cited by examiner

*Primary Examiner*—David O. Reip
(74) *Attorney, Agent, or Firm*—Clayton, Howarth & Cannon, P.C.

(57) ABSTRACT

A spine fixation apparatus and method including at least one longitudinal rod mounted parallel to the axis of the spine and having a plurality of stem clamps adjustably mounted to the longitudinal rod. Each stem clamp has a stem extending outwardly therefrom with the diameter of the stem being identical to the diameter of the longitudinal rod. A plurality of C-clamps are provided and are mounted to the stems and to the longitudinal rods. A plurality of bone pins are provided and are used to preliminarily mount the spinal fixation construct to the spine to allow the surgeon to determine by X-ray the accuracy of the construct with regard to the spine. A plurality of innovative bone screws are used to simultaneously anchor the C-clamps to the bone and to the respective stem and longitudinal rod. The bone screws are configured with a smaller diameter at the distal end having threads thereon for threadedly engaging the underlying bone. The bone screw includes a threaded shoulder for threadedly engaging the Cclamp to clamp the same to the stems and the longitudinal rod. The thread pitch is identical for both threaded sections of the bone screw. A second longitudinal rod can also be used to create the spinal implant construct and be coupled to the first longitudinal rod through a plurality of cross-link plates.

74 Claims, 3 Drawing Sheets

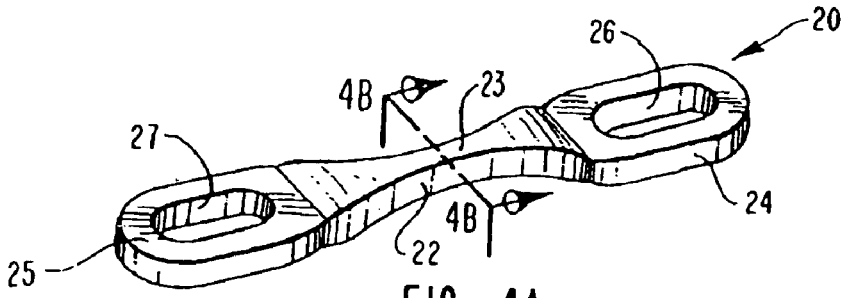
FIG. 4A
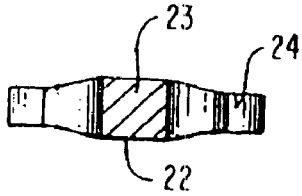
FIG. 4B
FIG. 5A
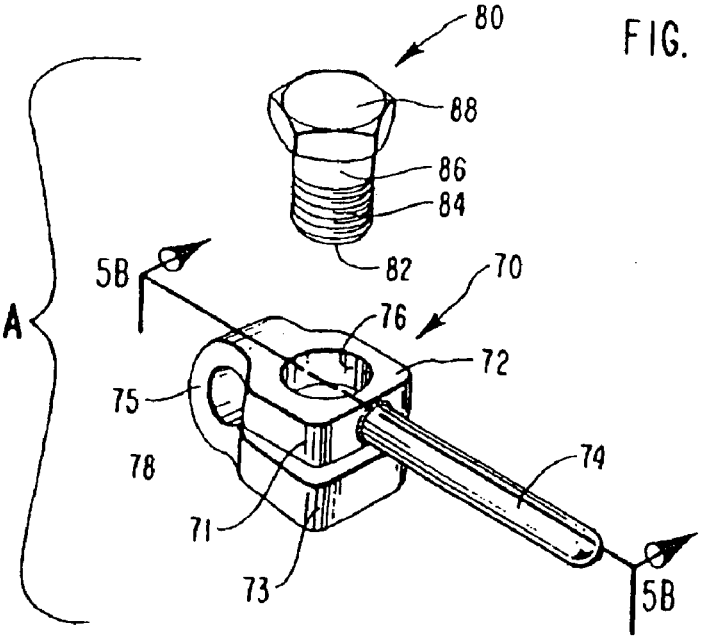
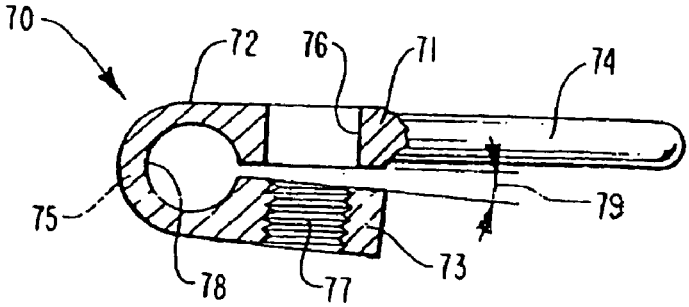
FIG. 5B

SPINAL FIXATION APPARATUS AND METHOD

Matter enclosed in heavy brackets [ ] appears in the original patent but forms no part of this reissue specification; matter printed in italics indicates the additions made by reissue.

RELATED APPLICATIONS

This application is a continuation-in-part application of my application Ser. No. 08/232,371, filed Apr. 25, 1994, for SPINAL FIXATION APPARATUS AND METHOD now U.S. Pat. No. 5,498,262 issued Mar. 12, 1996, which was a continuation-in-part application of Ser. No. 07/999,005 filed Dec. 31, 1992 for LUMBAR SPINE FIXATION APPARATUS AND METHOD now U.S. Pat. No. 5,306,275 issued Apr. 26, 1994.

BACKGROUND

1. Field of the Invention

This invention relates to medical instrumentation for achieving spinal fusion and, more particularly, to a novel, highly adaptive, and interchangeable component system and method for fixation of the lumbar spine and lumbosacral spine to aid the fusion of these spinal regions.

2. The Prior Art

The spine is a flexible, multi-segmented column that supports the upright posture in a human while providing mobility to the axial skeleton. The lumbar spine serves the functions of encasing and protecting vital neural elements and provides structural support for the body by transmitting the weight of the body through the pelvis to the lower extremities. Since there are no ribs attached to the lumbar spine, it has a relatively wide range of motion.

The spine is made up of bone, intervertebral discs, synovial joints with their articular cartilage, synovial capsules and, as part of the back, is surrounded by supporting ligaments, muscle, fascia, blood vessels, nerves, and skin. As in other areas of the body, these elements are subject to a variety of pathological disturbances: inflammation, trauma, neoplasm, congenital anomalies, disease, etc. In fulfilling its role in the back, the spine can be subjected to significant trauma which is assumed to play a dominant role in the etiology of low back pain, Trauma frequently results in damage at the upper end of the lumbar spine, where the mobile lumbar segments joint the less mobile dorsal spine. Excessive forces on the spine can not only produce life-threatening traumatic injuries, but may contribute to an increased rate of degenerative change. Degenerative changes tend to develop in the lower lumbar intervertebral discs, most commonly in the third decade. Osteoarthritis produces changes in the facet joints by middle age.

Certain severe cases of spine anomalies, such as a congenital scoliotic spine, or scoliosis developed as the result of diseases as cerebral palsy or muscular dystrophy, require surgery and instrumentation to correct or at least lessen the anomalous spine curvature. If exterior brace treatment has failed or a large progressive curve has developed without treatment, surgery can be used to diminish the curve. Severe scoliosis that goes untreated can cause deformities of the ribs that restrict the lung and later cause serious breathing problems, heart disease, or severe back pain.

One of the methods used to treat disabling pain, neurological compromise, or deformity produced by any of the above noted pathological conditions is fusion. The earliest spinal fusion techniques were basically posterior interlaminar fusions. Subsequently, later techniques led to the evolution of posterolateral techniques that allow a larger area for bone grafting and fusion. The relatively high rate of unsatisfactory results with traditional fusion techniques led to the evolution of lumbosacral fusion involving the use of hardware or instrumentation in an attempt to achieve stability and thus fusion or correction of deformity and stability followed by fusion. Internal spinal fixation increases rigidity and results in a high rate of fusion. This increased fusion rate and decreased pseudarthrosis rate gives better results and can significantly reduce postoperative pain and time for convalescence. Spinal fixation using instrumentation also allows correction of deformities and maintenance of that correction during consolidation by fusion. The primary considerations of the indications for spinal instrumentation are the magnitude of instability, the plane of deformity, and the available intact anatomy.

The past decade or two has seen an extensive development of internal devices for the lumbar and lumbosacral spine fixation. The following patents are typical of the patents in this field: Edwards (U.S. Pat. No. 4,569,338) teaches a sacral fixation screw having an aperture in the top for the engagement of a hook. Steffee (U.S. Pat. No. 4,648,388) teaches an apparatus for imposing a force on the spinal column. Howland et al. (U.S. Pat. No. 4,653,481) teach a spine fixation system having a plurality of screw clamp assemblies inserted through the pedicle and vertebral body and affixed to a rigid rod. Steffee (U.S. Pat. No. 4,719,905) teaches an apparatus including a rod, a plurality of clamps, and a plurality of fastener assemblies for securing the rod to a spinal column. Puno et al. (U.S. Pat. No. 4,805,602) teach an apparatus for the internal fixation of the spine, the apparatus including two sets of implants each consisting of a rod and a plurality of vertebral anchors. Heinig et al. (U.S. Pat. No. 4,887,595) teach a plate and screw system for maintaining the relative position of the spinal bodies of a spinal column. Sherman (U.S. Pat. No. 4,887,596) teaches a pedicle screw for use in internal fixation of the spin. Gotzen et al. (U.S. Pat. No. 4,944,743) teach an implantable fixation device having a support bar with jaw supports threadedly engaged to the support bar. Gaines, Jr. (U.S. Pat. No. 4,950,269) teaches a rod and fastener apparatus for connecting the rod to the vertebra of a spinal column. Krag et al. (U.S. Pat. No. 4,987,892) teach a pedicle screw and rod apparatus for spinal fixation. Cotrel (U.S. Pat. No. 5,005,562) teaches an implant for spinal fixation, the implant including a rod and pedicle screws and hooks mountable to the rod. Howland (U.S. Pat. No. 5,030,220) teaches an implantable spinal fixation system that uses a pedicle screw to secure the longitudinal rods to the spine. An improved locking system maintains the structural integrity of the construct. Cozad et al. (U.S. Pat. No. 5,074,864) teaches a mid-line clamp assembly for use in posterior spinal fixation. The clamp assembly includes inferior and superior clamp halves that are slideably interconnected. The clamp halves are engageable about the longitudinal rods. Asher et al. (U.S. Pat. No. 5,084,049) teach a pair of corrective devices for securement to a spinal column. Each corrective device includes a spine plate having a plurality of openings for receiving a fastener to connect the spine plate to a vertebra. Tsou (U.S. Pat. No. 5,122,131) teaches an orthopedic device for secure mechanical coupling to an elongated surgical rod. Dubousset (U.S. Pat. No. 5,147,360) teaches an osteosynthesis device for correction of spinal curvature wherein anterior and posterior rods are affixed to the vertebral bodies to apply the necessary corrective forces to the spinal column. Cotrel (U.S. Pat. No. 5,154,719) teaches an implant for osteosynthesis, the implant being in the form of a screw having a rod-receiving head. Mathews (U.S. Pat. No. 5,171,279) teaches a percutaneous fusion technique using superfascial internal fixation. Schlapfer (U.S. Patent No. 5,190,543) teaches a pedicle screw having a slotted head for receiving a support rod. Mehdian (U.S. Pat. No. 5,217,497) teaches an implant for fixing one segment of a spinal column to another segment, the implant being in the form of a screw having a slotted head to which a support rod is anchored. Krag et al. (U.S. Pat. No. 5,219,349) teaches a device for use in the controlled alignment of a fractured spine in conjunction with the Vermont Spinal Fixator. Ashman (U.S. Pat. No. 5,242,445) teaches an eyebolt having two shell-like portions for engagement to a spinal rod. Vignaud et al. (U.S. Pat. No. 5,261,907) teaches an interconnecting device able to lock two spinal osteosynthesis fasteners. Wagner (U.S. Pat. No. 5,334,203) teaches a medical construct using surgical rods and connectors. The connector includes a plate with a pair of double hook bolts to secure the plate to the surgical rods. Yuan et al. (U. S. Pat. No. 5,352,225) teach a dual-tier spinal clamp locking and retrieving system. Jeanson et al. (U.S. Pat. No. 5,360,429) teach a device for straightening, fixing, compressing, and elongating the cervical spine. Lahille et al. (U.S. Pat. No. 5,380,325) teaches a consolidated rod and plural members such as pedicular screws and vertebral claws. Acromed Corp. (European Patent Application Publication Number 0 553 424 A1) teaches a plurality of screw-like fasteners mounted to individual vertebrae and interconnected by a longitudinal rod.

The most common rationale for using such devices is to reduce the incidence of pseudarthrosis after bone grafting. Another rationale (typically for trauma management) is to maintain intervertebral alignment to protect the neural elements until healing occurs. Yet another rationale is to provide fixation for correction of severe anomalous spine curvature due to severe scoliosis or other deformity which threatens life or health.

One of the early fixation methods involved the placement of screws obliquely across each facet joint involved in the grafting. However, the pseudarthrosis rate for this procedure was unacceptably high. Numerous other types of devices that variously include plates, wires, rods, bolts, hooks, and screws have evolved since that time and have resulted in a plethora of devices and instrumentation apparatus for use by the orthopedic surgeon to accomplish spinal fixation. Some of these fixation apparatus and methods require multiple adjustments to the longitudinal rods in order to adapt to specific anatomy. Although not provided by all these devices, the ideal spinal fixation apparatus would provide internal alignment and fixation not just in any one of various planes of movement, but in a full, three-dimensional construct where subject fixation apparatus is simplified, low profile, and easily manipulated and adjusted by the surgeon to allow for anatomy variations, while at the same time providing an extremely rigid construct upon tightening of connection points.

As shown herein before, numerous patents have been issued for various types of spine fixation devices. These devices employ different mechanical apparatus for enabling the surgeon to selectively adjust the alignment of the patient's spine and then to secure that alignment with the spine fixation device. Most of these devices are relatively difficult to adjust and require undue surgical time in their implantation. Further, due to the wide variation in spinal dimensions and availability of suitable attachment sites, most devices have limited application. Further still, these devices do not allow the surgeon to easily manipulate and position the bone screws prior to final tightening of the device.

Another characteristic inherent in prior art spinal fixation apparatus are the manipulation restrictions due to screw thread configuration. Generally, prior bone screw thread configurations have been either single thread pitch (number of threads per unit of length) over the entire length of the bone screw, which requires that the clamping device be engaged from the beginning of the threading process, or other complex configurations involving set screws, or other devices which are either cumbersome to adjust and tighten or cause undue disruption of the cancellous bone tissue. Bone screws of differing thread pitch have an advantage that final positioning is not required until just prior to final tightening of the device, but still have the disadvantage of, due to the discrepancy in the thread pitch, causing the bone screw to create undue coaxial pressure on the lattice-like cancellous tissue of the bone, thereby increasing possible shearing or undue disruption of bone tissue.

A further characteristic of prior bone screw configurations is that the thread angle of the top surface of the thread is not orthogonal relative to the axis of the screw, thereby lessening gripping strength. Specifically, increasing the angle of the thread surface proximal to the bone screw head such that the angle is nearly orthogonal relative to the bone screw axis, correspondingly decreases the lateral forces imposed by that thread on bone tissue by the tightening process.

In view of the foregoing, it would be a significant advancement in the art to provide a spinal fixation apparatus and method that was highly interchangeable, simplified, and would increase the ease of installation and adjustment while decreasing the total time required for surgical implantation and fixation. It would also be an advancement in the art to provide a spinal fixation apparatus and method that would utilize a multi-diameter threaded bone screw of the same thread pitch for all diameters, such that, upon tightening, would have no net increase in axial pressure on the cancellous bone tissue due to thread pitch variance. An even further advancement in the art would be to provide a bone screw with a modified thread configuration such that the top surface of the thread is nearly orthogonal to the axis of the bone screw, thereby decreasing the lateral pressure on the cancellous bone tissue, subsequently lessening the likelihood of shearing upon tightening. Such a novel spinal fixation apparatus and method is disclosed and claimed herein.

BRIEF SUMMARY AND OBJECTS OF THE INVENTION

This invention relates to a novel spinal fixation apparatus and method and includes specially designed C-clamps, cross-link plates, stem clamps, bone screws, and longitudinal rods—all of which are used for spinal fixation. The various components are designed to be interchangeable, highly adaptable, and easily manipulated by the surgeon at time of implantation. The bone screws provide greater gripping strength and ease of implantation.

It is, therefore, a primary object of this invention to provide improvements in spinal fixation apparatus.

Another object of this invention is to provide improvements in the method for fixation of a spine for fusion.

Another object of this invention is to provide a spinal fixation apparatus that has interchangeable components, is greatly simplified, and has infinite capability to locate bone screws in any orientation without the necessity of bending the longitudinal rods thereby also allowing the use of more biocompatible materials, such as titanium, which exhibits less image interference (scatter) on a CT scan.

Another object of this invention is to provide bone screws and C-clamps that can be used on either the left or right side of the longitudinal rod, as well as directly on the longitudinal rod when situation dictates.

Another object of this invention is to provide a cross-link plate with a squared cross-section at its midriff to allow the cross-link plate to be bent or twisted to adapt to specific anatomy and increase ease and accuracy of implantation.

Another object of this invention is to provide a C-clamp which possesses two opposing indentations for secure accommodation of a manipulation tool during implantation and tightening of the various components of the construct.

Another object of this invention is to provide a bone screw with first and second threaded sections of different diameters but with the same thread pitch.

Another object of this invention is to provide a bone screw that can be positioned prior to tightening without creating undue coaxial forces on the cancellous bone tissue.

Another object of this invention is to provide a bone screw thread configuration that supplies greater gripping strength due to the top surface of the thread being nearly orthogonal relative to the axis of the bone screw.

These and other objects and features of the present invention will become more readily apparent from the following description in which preferred and other embodiments of the invention have been set forth in conjunction with the accompanying drawing and appended claims.

BRIEF DESCRIPTION OF THE DRAWING

FIG. 4A is a perspective view of the cross-link plate;

FIG. 4B is a cross-sectional view of the cross-link plate of FIG. 4A taken along lines 4B—4B of FIG. 4A;

FIG. 5A is an exploded perspective view of a stem clamp and bolt;

FIG. 5B is a cross-sectional view of the stem clamp of FIG. 5A taken along lines 5B—5B of FIG. 5A.

DETAILED DESCRIPTION OF THE PREFERRED EMBODIMENT

Figure 1:
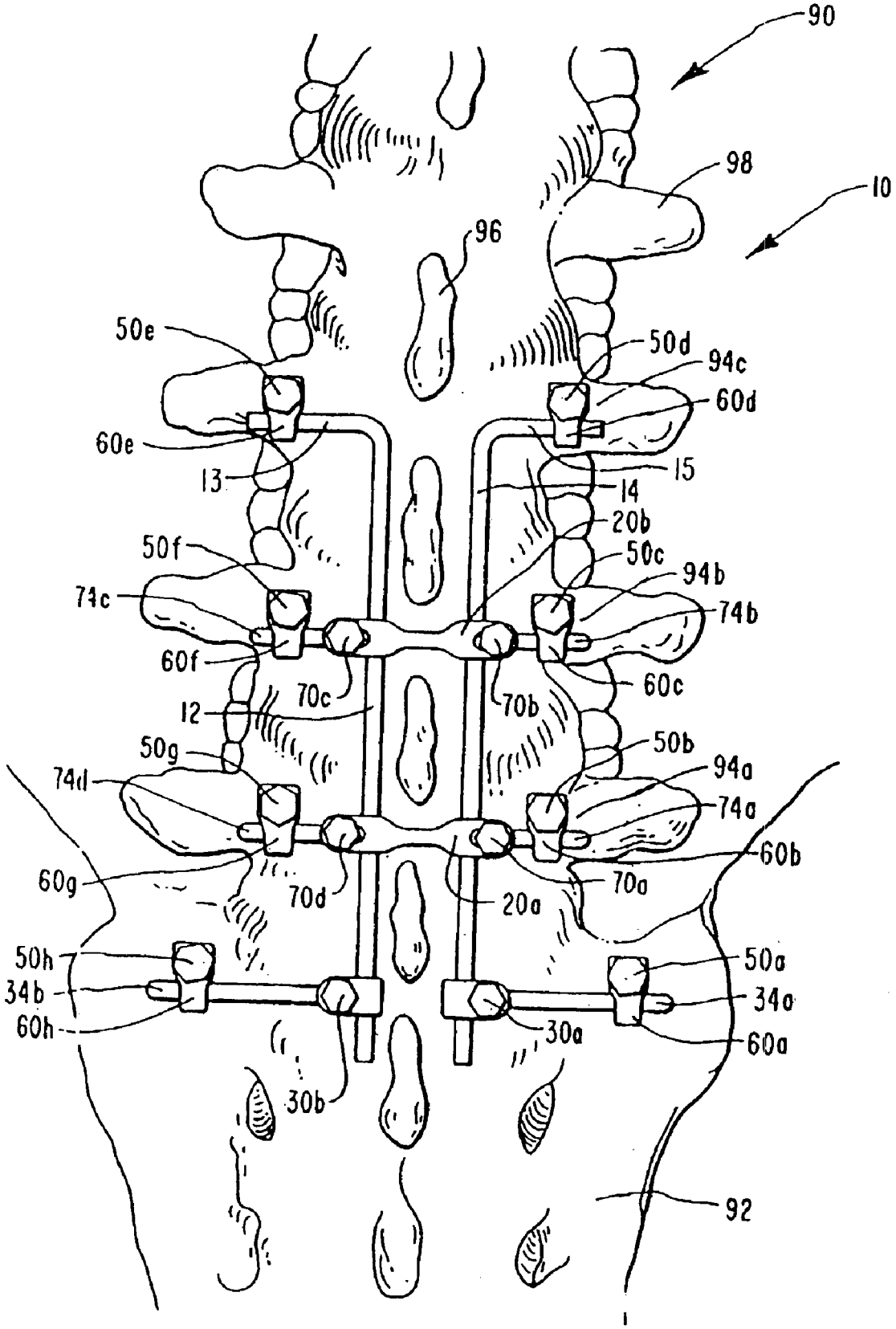
FIG. 1 is a plan view of the spine fixation apparatus of this invention shown in the environment of a portion of the lumbosacral spine.

The invention is best understood from the following description with reference to the drawing wherein like parts are designated by like numerals throughout and taken in conjunction with the appended claims.

General Discussion

The underlying rationale for spinal fusion is to (a) restore the integrity of the spine or to replace missing bone stock, i.e., fracture, tumor, infection; (b) produce an arthrodesis that will suppress undesired movement between two or more bony elements that are the source of pain; and (c) maintain correction of spinal deformity or to prevent progression of deformity. In general, this arthrodesis is produced by using a bone graft that will heal and mature thereby binding the involved elements intimately. Arthrodesis requires in most instances a period of immobilization to achieve this end. Importantly, the key factor in predicting successful fusion is the amount of instability; that is, if instability is moderate and bone stock good,the proportion of easy primary fusion will increase. This goal is readily accomplished using the unique apparatus and method of this invention.

Since fusion is performed in the region of the unstable spinal segment that one wants immobile, the use of the internal fixation apparatus increases rigidity and gives a higher rate of fusion. This resultant increased fusion rate and decreased pseudarthrosis rate gives better results and can ease postoperative management regimens. Therefore, spinal instrumentation allows correction of deformity and rigid fixation of that correction during consolidation by fusion.

The unique spinal fixation apparatus and method of this invention enables the surgeon to securely immobilize the desired number of lumbar vertebrae thereby providing a stable condition for the ingrowth of bone tissue to achieve true spinal fixation. Importantly, the spinal fixation components of this invention are configured to reduce, if not eliminate, the incremental movement of micromotion between the various components. The angular orientation of the bone screw placement is designed to achieve optimal fixation between the device and the vertebrae to which it is affixed. The bone screws are specifically designed pass through the C-clamp without engaging the threads of the C-clamp while tapping into the pedicle, thereby allowing the surgeon to more accurately position and adjust the apparatus prior to tightening. The pedicle screw is anchored securely through pedicle into the vertebral body and simultaneously secures the C-clamp to engage the side arm portion of the stem clamp or the longitudinal rod in a tight, non-release fashion. This invention also provides the surgeon with greater ease of implantation of the fixation apparatus thereby decreasing the operative trauma and the postoperative convalescence.

My innovative spinal fixation apparatus centers around at least one longitudinal rod to which a plurality of bone screw and C-clamp combinations and stem clamps are attached. More than one longitudinal rod cam be employed in assembling the construct of my invention and in such circumstances cross-link plates are provided to lend structural support between the two longitudinal rods. The C-clamp is configured to be slideably mounted to the longitudinal rod and securely anchored thereto by being clamped together upon threaded engagement by the bone screw. The bone screw is configured with a first, distal set of threads having a first, smaller diameter and a second, proximal set of threads having a second, larger diameter. The thread pitch for the first set of threads is identical to the second set of threads. The C-clamp has a lower jaw having threads therein which correspond to the second set of threads on the bone screw. This feature allows the bone screw to be passed through the C-clamp and into threaded engagement with the underlying bone without engaging the C-clamp. However, once the bone screw has been suitably engaged into the bone the surgeon is then able to securely engage the C-clamp with the bone screw thereby securely engaging the C-clamp to either the longitudinal rod or the side arm of the stem clamp while tightly affixing the same to the bone. The identical thread pitch on both sets of threads of the bone screw means that as the bone screw engages and tightens the C-clamp, the continued axial movement of the bone screw into the bone is at the identical rate as prior to engagement of the C-clamp. This means that there is negligible change in the axial distance travelled by the bone screw during each rotation of the bone screw thereby effectively eliminating the gouging or disruption of the adjacent bone structure that would otherwise occur if one were using a prior art bone screw having a first thread pitch for the bone portion of the bone screw and a second thread pitch for engagement with the C-clamp. The end result is that my innovative bone screw not only secures the C-clamp securely against the longitudinal rod or the side arm of the stem clamp but it also is simultaneously sealed more snugly into the underlying bone thereby significantly reducing the possibility of micromotion between the bone screw and the bone. This in turn significantly reduces postoperative pain and speeds healing.

Importantly, the overall dimensional profile of the construct created from my innovative bone screw, C-clamp, stem clamp, and longitudinal rod combination is lower or, more specifically, implantable closer to the spine where it is thereby able to more securely hold the spine in the orientation determined by the surgeon. Further, the low profile means that there is a significant reduction in the moment arm as represented by the distance between the bone of the spine and the longitudinal rod. Reducing this moment arm significantly lowers the bending forces imposed on the bone by the forces resisted by the longitudinal rods.

Another important feature provided by the various components of the construct of my invention is that the surgeon is provided with an infinite selection of angles by which the bone screw can be directed into the bone. This feature is particularly advantageous in that the pedicle orientation varies from patient to patient and even between the different vertebra on the same spine. Angular selection for the direction of insertion of the bone screw is provided by the fact that the stem camp is rotatable a full 360° about the longitudinal rod while the C-clamp is likewise rotatable a full 360° about either the stem or side arm of the stem clamp or the longitudinal rod. Accordingly, the surgeon is able to selectively rotate both the stem clamp and the C-clamp to thereby achieve the preselected angular orientation of the bone screw into the underlying bone structure.

In addition to the foregoing features by my invention, I also provide a bone pin system for temporarily securing the spinal fixation apparatus in position on the spine to permit me to analyze the construct and its spinal placement through the use of X-ray analysis. Once X-ray analysis has shown that all of the elements of the construct are properly positioned it is a simple procedure to merely replace each bone pin with a bone screw.

Possibly the most important feature of the innovative spinal fixation apparatus of my invention is that the entire construct can be mounted to the spinal column with the bone screws properly placed prior to the final tightening of the various C-clamps and stem clamps. This final tightening procedure is readily accomplished in the absence of unacceptably altering the final orientation of the construct and without imposing distortional stresses on the construct.

DETAILED DESCRIPTION

Referring now to FIG. 1, the unique spinal fixation apparatus of this invention is shown generally as construct 10 mounted to the lumbar region of a spine 90. Spine 90 includes a sacrum 92 and a plurality of vertebra 94a–94d. Vertebra 94a–94d each include an upwardly extending spinous process 96 along with a transverse process 98 extending outwardly on each side, only one spinous process and transverse process being numbered herein for sake of simplicity in presenting this invention. A pair of longitudinal rods 12 and 14 are aligned on each side of spinous process 96 to provide longitudinal support to spine 90. Longitudinal rods 12 and 14 are shown here as being the same diameter, though differing diameter longitudinal rods could be accommodated in the assembly of construct 10 if determined to be advantageous by the surgeon (not shown). The most likely configuration selected would be to utilize longitudinal rods 12 and 14 of the same diameter to facilitate interchangeability between components. Longitudinal rods 12 and 14 are shown with a right angle bend to illustrate a unique feature of this invention that simplifies construct 10 as will be discussed more fully hereinafter. This orthogonal bend in longitudinal rods 12 and 14 creates side arms 13 and 15, respectively, which provide an anchor point for anchoring that end of longitudinal rods 12 and 14 to spine 90, *and, as shown in FIG. 1, said side arms 13 and 15 constitute lateral extensions extending from a midline of longitudinal rods 12 and 14, respectively. Accordingly, side arms 13 and 15, as suggested and implied herein, can be pre-formed by the manufacturer and thus not formed responsive to any particular patient's anatomical features. In such a case, the side arms 13 and 15 are not made for the primary purpose of deforming the longitudinal rods 12 and 14 to the curvature or shape of the spine 90, but rather simply to provide an anchoring point for attachment to the spine 90 as noted above and by the depiction in FIG. 1 of the abrupt bends that form said side arms 13 and 15. As also shown in FIG. 1, the longitudinal rod 12 includes a primary, longer portion and a shorter portion that is the side arm 13, thereby forming an "L" shape.*

Construct 10 is assembled from two lengths of stem clamps, stem clamps 30a–30b and stem clamps 70a–70d, in combination with cross-link plates 20a and 20b, C-clamps 60a–60h, and bone screws 50a–50h, all of which will be discussed more fully hereinafter. Stem clamps 30a and 30b are each affixed to the respective lower end of longitudinal rods 12 and 14 and provide the mechanical structure for enabling C-clamps 60a and 60h along with their respective bone screws, bone screws 50a and 50h to secure these elements to the sacrum 92. Correspondingly, stem clamps 70a–70d in combination with C-clamps 60b–60g and bone screws 50b–50g, respectively, provide the necessary securement of longitudinal rods 12 and 14 to vertebra 94a–94c, respectively. Cross-link plates 20a and 20b provide the necessary bridging mechanism between longitudinal rods 12 and 14 by being clamped thereto by stem clamps 70a–70d, respectively, when stem clamps 70a–70d are secured to longitudinal rods 12 and 14, respectively. Stem clamps 30a–30b and stem clamps 70a–70d are identical with the exception of length of the respective side arm and could thereby accommodate an additional cross-link plate 20 should the situation dictate.

It is important to emphasize at this juncture that the versatility of construct 10 is significantly enhanced by the fact that bone screws 50a–50h are capable of being directed in any preselected angular orientation into the particular underlying bone structure of spine 90. For example, the proper angular orientation of bone screws 50d and 50e is achieved by rotating the respective longitudinal rod 12 and 14 to bring side arm 13 and 15 into the desired placement relative to spine 90. Correspondingly, C-clamps 60d and 60e are rotated about side arms 13 and 15 respectively, to correctly orient the angular position of bone screws 50d and 50e, respectively, with spine 90. Similarly, C-clamps 60a–60c and 60f–60h are rotatable a full 360° about the respective stems of stem clamps 30a, 30b, and 70a–70d while stem clamps 30a, 30b, and 70a70d are also rotatable a full 360° about longitudinal rods 12 and 14, respectively. This feature allows the surgeon to have an infinite choice for the angular orientation of the respective bone screws, bone screws 50a–50c and 50c–50g.

Figure 2A:
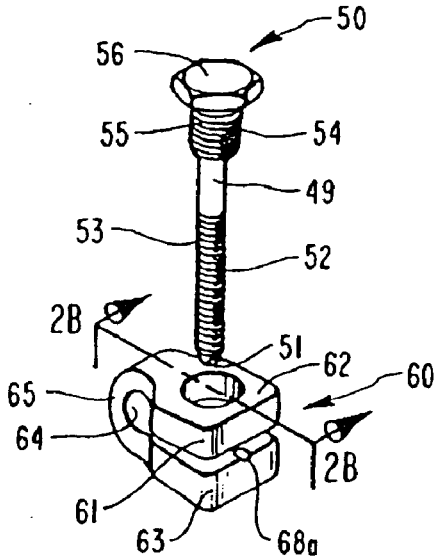
FIG. 2A is an exploded perspective view of a bone screw and C-clamp.
Figure 2B:
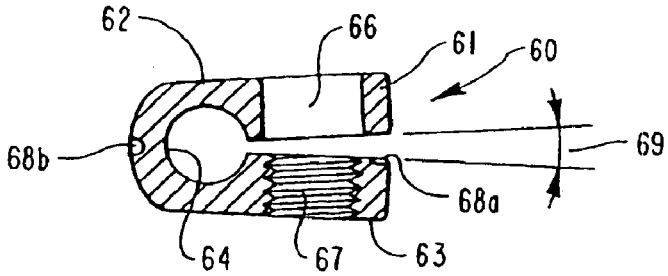
FIG. 2B is a cross-sectional view of the C-clamp of FIG. 2A taken along lines 2B—2B of FIG. 2A.
Figure 3A:
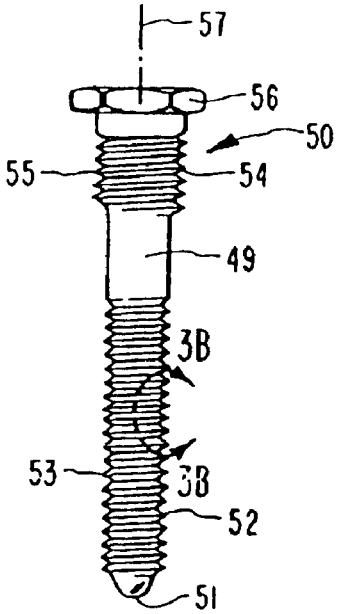
FIG. 3A is a side elevation of the bone screw of FIG. 2A.
Figure 3B:
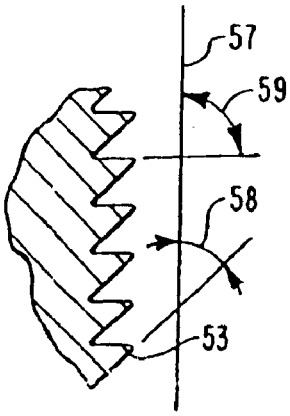
FIG. 3B is a greatly enlarged, fragmentary, cross-sectional view of the threads on the bone-engaging portion of the bone screw of FIG. 3.

Referring now to FIGS. 2A, 2B and 3, C-clamp 60 is shown herein in combination with bone screw 50. C-clamp 60 includes a clamp body 62 having an upper jaw 61 and a lower jaw 63 interconnected by a cylindrical sidewall 65. Cylindrical sidewall 65 defines a lateral throughbore 64 through clamp body 62. Lateral throughbore 64 is configured to slidingly receive stem 74 (FIGS. 5A and 5B) or side arms 13 and 15 of longitudinal rods 12 and 14 (FIG. 1), respectively. C-clamp 60 includes a transverse-throughbore 66, through upper jaw 61 and lower jaw 63. The bottom portion of transverse throughbore 66 in lower jaw 63 is configured with threads 67 to engage large diameter threads 54 of bone screw 50. Two opposing indentations 68a and 68b are configured for secure accommodation of a manipulation tool (not shown) by the surgeon during manipulation and tightening of C-clamp 60.

Bone screw 50 is configured with a bolt head 56, an enlarged neck 54, a collar 49 and shaft 52 extending downwardly therefrom. Neck 54 is threaded with threads 55 while shaft 52 is threaded with threads 53. Collar 49 is characterized by the absence of threads and has an outer circumference that approximates the outer circumference of threads 53. Bone screw 50 terminates downwardly in a blunt tip 51 at its distal end. Transverse throughbore 66 of C-clamp 60 is sufficiently large to allow the smaller diameter of threads 53 and collar 49 to pass freely through transverse throughbore 66 and, particularly, threads 67 of lower jaw 63 in a nonbinding relationship. I have found that the smooth profile of collar 49 is particularly useful in that it minimizes any tendency for threads 53 to bind with threads 67 during the final stages of mounting bone screw 50 into C-clamp 60. Their tendency toward thread binding occurs due to slight angular offsets that may occur upon the final assembly of bone screw 50 into C-clamp 60. Collar 49 thereby provides a smooth surface against which threads 67 can not bind.

The larger diameter threads 55 on neck 54 also pass through the portion of transverse throughbore 66 in upper jaw 61 freely in a nonbinding relationship until engaging threads 67 in lower jaw 63. The diameter and pitch of threads 55 are configured to threadedly engage threads 67 to bring bolt head 56 into abutment against upper jaw 61. Further tightening of bone screw 50 will simultaneously engage bone tissue (not shown) while forcing the closing of upper jaw 61 downwardly against lower jaw 63. Accordingly, side arm 74 or longitudinal rods 12 or 14 residing in lateral throughbore 64 will be securely engaged by this clamping action of C-clamp 60. Importantly, the thread pitch is identical for all of threads 53, 55, and 67.

The multiple diameter configuration of bone screw 50 as to neck 54 and shaft 52 increases flexibility in installation and adjustment while decreasing the total time required for surgical implantation and fixation by allowing the surgeon to partially position bone screw 50 in the pedicle of the vertebra 94 or sacrum 92 (FIG. 1), creating multiple elements of construct 10, then returning to each bone screw 50 or side arm clamps 30 and 70 (FIG. 1) for final adjustment and consolidation in a tight, non-release fashion. The match of thread pitch of both smaller diameter threads 53 on shaft 52 and the larger diameter threads 55 on neck 54 accommodates the tightening of the bone screw 50 into C-clamp 60 as well as the underlying bone structure without changing the axial pressure on the lattice-like cancellous bone tissue that would otherwise occur if there were a thread pitch variance as in prior art devices.

Bone screw 50 includes a unique thread configuration of the top surface of thread 53 in that it is undercut or nearly orthogonal to axis 57 of bone screw 50 as shown by angle 59. The bottom surface of thread 53 resides at an acute angle 58. This latter angle more nearly approximates the angular surfaces of threads 55. During the tightening of bone screw 50 into the pedicle bone and subsequent clamping with C-clamp 60, the top surface of thread angle 59 serves to decrease the lateral pressure on the cancellous bone tissue in which bone screw 50 is implanted, thereby increasing the gripping capability while decreasing likelihood of disruption of cancellous bone tissue. In essence, this top surface acts to undercut and thereby more securely embed threads 53 into the bone structure.

With specific reference to FIG. 2B, C-clamp 60 is shown with an angular offset 69 in the relationship between upper jaw 61 and lower jaw 63. Angular offset 69 is in the range of one to ten degrees and allows bolt head 56 to strike the elevated edge of upper jaw 61 first and then as threads 55 on neck 54 continue to tightly engage threads 67 in lower jaw 63 cause upper jaw 61 to be pressed downwardly into a parallel orientation with lower jaw 63. This latter configuration allows the bottom face of bolt head 56 to rest uniformly against the top face of upper jaw 61 for a more secure engagement between bolt head 56 and upper jaw 61. Accordingly, angular offset 69 is designed to accommodate the necessary closure motion between upper jaw 61 and lower jaw 63 in order to securely clamp either stem 74 or longitudinal rod side arms 13 and 15 within the confines of lateral throughbore 64 while simultaneously providing a full 360° contact surface for bolt head 56 against upper jaw 61.

Referring now to FIGS. 4A and 4B, cross-link plate 20 is shown more clearly and includes a shank 22 having an eyelet 24 at one end and an eyelet 25 at the other end. Shank 22 is formed with a waist-like configuration having a square profile 23 as shown in the cross-sectional view of FIG. 4B. The squared, cross-section at profile 23 of shank 24 allows the cross-link plate 20 to be deformably shaped into an upwardly convex curvature or otherwise twisted or bent, to accommodate specific anatomical features encountered during implantation thereby increasing the ease and accuracy of implantation and fixation of construct 10 to spine 90. This feature further allows the surgeon to place longitudinal rods 12 and 14 closer to spine 90 since cross-link plate 20 can be deformably configured to achieve this placement. In addition to other adjustments, elongation of slots 25 and 27 in eyelets 24 and 25, respectively, provides the surgeon with a greater degree of axial adjustability in securing cross-link plate 20 between longitudinal rods 12 and 14. Further, cross-link plate 20 can be mounted at each stem clamp, stem clamps 30 and 70, located along the length of construct 10.

Referring now to FIGS. 5A and 5B, stem clamp 70 is shown with bolt 80. Stem clamp 30 (FIG. 1) is essentially identical to stem clamp 70 the only difference being the relative length of the respective stems 34 and 74. Stem clamp 70 includes a clamp body 72 having a generally C-shaped configuration with an upper jaw 71 and a lower jaw 73. Lower jaw 73 is angularly offset from upper jaw 71 by an angle between one and ten degrees as shown by angle 79. Upper jaw 71 is connected to lower jaw 73 through a cylindrical sidewall 75 having a lateral throughbore 78 therethrough. Lateral throughbore 78 slidingly receives and ultimately engages longitudinal rod 12 or 14 as will be discussed hereafter. Importantly, cylindrical sidewall 75 is provided with a limited degree of resiliency between upper jaw 71 and lower jaw 73 so that when these jaws are urged together the subject clamping action of longitudinal rod 12 or 14 in lateral throughbore 78 can occur. Clamp body 72 includes a transverse bore 76 through upper jaw 71 and lower jaw 73. The portion of transverse bore 76 through upper jaw 71 is unthreaded so that bolt 80 can be passed through upper jaw 71 freely in a nonbinding relationship to threadedly engage threads 77 (FIG. 4B) in lower jaw 73. Specifically, bolt 80 is configured with a shaft 82 having a bolt head 88, a neck 56 and threads 84. Threads 84 are configured to threadedly engage threads 77 to bring bolt head 88 into abutment against upper jaw 71. Further tightening of bolt 80 in stem clamp 70 forces the closing together of upper jaw 71 toward lower jaw 73 to eliminate angle 79 so that longitudinal rod 12 or 14 residing in lateral throughbore 78 will be securely engaged by this clamping action. Accordingly, stem clamp 70 is similar to C-clamp 60 in that it is also configured with an angular offset similar to angular offset 69 (FIG. 2B) for the same purpose. *Additionally, as used herein, the concept of "intercoupling" vertebrae to one another, in accordance with the plain and ordinary meaning of the term "intercouple," means to connect said vertebrae together with an interconnecting structure such as the longitudinal rods 12 and 14 and the C-clamps 60 and the stem clamps 30 and 70, or any other suitable interconnecting structure.*

Figure 6:
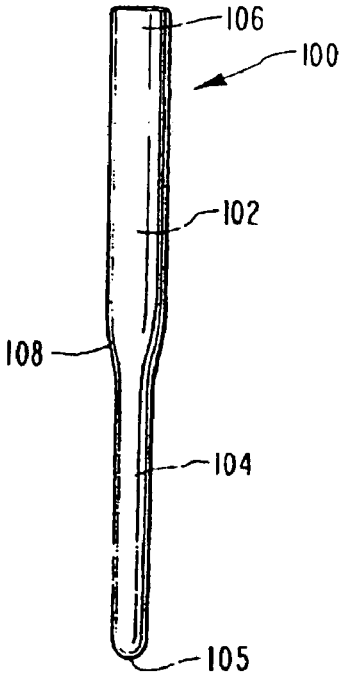
FIG. 6 is a perspective view of a bone pin for use in temporarily holding the position of the construct of this invention.

Referring now to FIG. 6, the bone pin for use in temporarily mounting construct 10 to spine 90 is shown at 100 and includes a shaft 102 having a diametrally enlarged portion which serves as a handle 106 and a diametrally reduced portion which serves as a pin 104. Pin 104 terminates distally in a blunt tip 105. Bone pin 100 is specifically designed to be positioned temporarily in transverse throughbore 66 of C-clamp 60 (FIG. 2A) with pin 94 extending downwardly into the hole (not shown) reamed into spine 90, the hole in spine 90 being intended for the threaded engagement therewith by bone screw 50 (FIG. 3). This feature allows the surgeon to use a plurality of bone pins 100 to temporarily secure construct 10 to spine 90 and then suitably analyze all features of construct 10 in its relationship to spine 90 by using conventional X-ray analysis techniques. This unique feature of my invention significantly improves the fixation of spine 90 reducing the misalignment of any of the elements of construct 10 relative to spine 90. Further, bone pin 100 provides a simple technique for enabling the surgeon to quickly and accurately determine the correct placement of bone pin 100 prior to insertion of bone screw 50 into the underlying bone structure of spine 90.

The Method

Construct 10 is affixed to spine 90 by a very straightforward procedure. Specifically, all of the holes to receive bone screws 50a–50h are sited and then selectively reamed. Thereafter, longitudinal rod 12 having the predetermined length and diameter is selected. Stem clamp 30b is attached to the end thereof and C-clamp 60h is mounted to stem 74 (FIGS. 5A and 5B). Bone screw 50h is then embedded in sacrum 92 to loosely hold stem clamp 30b and longitudinal rod 12 to sacrum 92. During this procedure, longitudinal rod 12 is oriented upwardly out of the surgical incision (not shown). The surgeon has previously slipped the preselected number of stem clamps 70 on longitudinal rod 12. Bone pin 100 is then passed through C-clamp 60e and inserted in the pedicle within vertebra 94c to loosely hold C-clamp 60e to spine 90. Longitudinal rod 12 is then slidingly adjusted to pass through throughbore 64 of C-clamp 60e. In this manner, longitudinal rod 12 is oriented relative to spine 90. The next step is for the intervening stem clamps 70c and 70d to be mounted to spine 90 using C-clamps 60f and 60g in combination with a plurality of bone pins 100. Longitudinal rod 14 is also positioned on spine 90 following the identical procedure used for longitudinal rod 12.

With most of the elements of construct 10 held in place on spine 90 through the use of a plurality of bone pins 100 the surgeon is able to use X-ray techniques to accurately determine the correct placement of construct 10 as well as bone screws 50. This is particularly advantageous since bone screws 50 have yet to be mounted to spine 90. Once it has been determined that all elements of construct 10 are suitably positioned on spine 90 the surgeon is readily able to secure construct 10 to spine 90 in this predetermine position by simply removing and replacing one by one each of bone pin 100 with a bone screw 50. Thereafter, cross-link plates 20 are mounted to stem clamps 30 and 70 and final securement thereof is accomplished by tightening bolt 80 therein. Importantly, cross-link plates 20a and 20b are suitably shaped as described hereinbefore and then mounted between the respective pairs of stem clamps 70a–70d by having bolts 80 (FIG. 4A) secured to stem clamps 70a–70d. If further stabilization is required, an additional cross-plate 20 could be installed between stem clamp 30a and stem clamp 30b.

With each of bone screws 50a–50d in place along with stem clamps 30a and 30b and stem clamps 70a–70d, the surgeon is now ready to make any final adjustment to construct 10 and then suitably tighten all of these elements as needed to achieve the desired fixation of spine 90 with the spinal fixation apparatus of construct 10 without imposing undesirable forces on spine 90. Specifically, if one has ever attempted to achieve final tightening of two moveable elements through the use of a set screw system, one has experienced the fact that the act of tightening almost always results in a rotational movement being imparted by the set screw against the element being engaged by the set screw. To compensate for this notorious characteristic of a set screw, it is customary for the operator to adjust the orientation of the movable element so that when the set screw has been suitably tightened (and has thereby rotated the element to, hopefully, its final position) the element will be set at its desired position. Precise final alignment of the two elements using the prior art set screw system is, therefore, a matter of experience coupled with extensive trial and error. However, with respect to the spinal support system provided by construct 10 presented herein, such a final fixation system for the various components of construct 10 is unnecessary. In particular, it is poor medical practice to implant a spinal fixation device in a patient in such a way as to impose unacceptable forces on the spine as a result of the final position setting of the components in the spinal fixation device. Construct 10 eliminates all of these problems by the unique design of its components. Stem clamps 30 and 70 impart absolutely no rotational forces against the particular element engaged thereby. Additionally, the clamping action of C-clamps 60 involve the constriction of the respective rod elements in the absence of any rotational forces being imposed on the rod element. As further assistance and security during tightening, two opposing indentations 68a and 68b on C-clamp 60 (FIG. 2B) are configured to accommodate engagement by a manipulation tool (not shown) during adjustment and tightening.

Construct 10 provides numerous advantages in the art of spine fixation in that it readily allows the surgeon to adapt the final configuration to any anatomical condition encountered on spine 90. Specifically, the combination of stem clamps 30 and 90 in conjunction with C-clamps 60 provides the surgeon with unlimited ability to direct the placement of bone screw 50 at any angle in both the sagittal plane and the coronal plane. Further, stems 34 and 74 permit significant translational placement of bone screw 50. These features are very advantageous since the entry angle as well as the entry point for bone screw 50 will vary from position to position on spine 90. The end result is that I have effectively eliminated the need to bend or shape longitudinal rods 12 and 14. The only bending or contouring required during the surgical procedure is that of cross-link plate 20. This shaping is easily accomplished by clasping each of eyelets 24 and 25 in the jaw of a suitable tool and applying the necessary bending/twisting forces on shank 22.

In summary, construct 10 provides a distinct advantage to the surgeon (not shown) in that it allows the surgeon to create any suitable spatial relationship between construct 10 and spine 90 for the purpose of packing bone graft (not shown) therebetween while at the same time providing a very strong, rigid, spinal support system. This advantage is possible through the use of the innovative clamping system involved in stem clamps 30 and 70. Not only do these clamping devices provide a very solid linkage between components in construct 10, but they also provide a highly advantageous degree of assembly flexibility in assembling construct 10. Specifically, bone screws 50a–50h are almost never secured to spine 90 in a direction that is perpendicular to a plane represented by the axis of longitudinal rod 12 and side arm 13, for example. The ideal placement of bone screws 50a–50h is almost always at some angular offset so that the various components of construct 10 are particularly useful in that they accommodate the precise placement of bone screws 50a–50h regardless of the respective angular orientation. Further, once in place, the entire spinal support apparatus of construct 10 is then securely affixed in the final configuration to thereby provide a rigid spinal support system for spine 90. This latter feature is important and is made possible by the various elements that constitute construct 10.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A spinal fixation apparatus comprising:

a longitudinal rod;

a plurality of stem clamps mounted to said longitudinal rod, each of said stem clamps comprising a clamp body having a stem extending outwardly therefrom and an upper jaw and a lower jaw, said upper jaw being resiliently joined to said lower jaw through a cylindrical sidewall, said cylindrical sidewall forming one portion of a lateral throughbore through said clamp body for slidingly receiving said longitudinal rod in clamping relationship, said clamp body including a transverse throughbore passing through said upper jaw and said lower jaw, the portion of said transverse throughbore through said lower jaw having threads therein, said stem clamp including a bolt for passing through said transverse throughbore and threadedly engaging said threads in said lower jaw thereby compressing said upper jaw toward said lower jaw to securely anchor said stem clamp to said longitudinal rod;

a plurality of C-clamps mounted to said stems and to said longitudinal rod, each of said C-clamps including a clamp body having an upper jaw and a lower jaw resiliently connected to said upper jaw through a cylindrical sidewall, said cylindrical sidewall forming a lateral throughbore through said clamp body for selectively receiving said longitudinal rod and said stems, said clamp body including a transverse throughbore through said upper jaw and said lower jaw, said transverse throughbore including threads in said lower jaw; and a bone screw for selectively securing said C-clamp to said longitudinal rod and said stem, said bone screw also mounting said C-clamp to bone, said bone screw having an elongated screw body and a screw head, said screw body having a distal end and a proximal end with said proximal end being adjacent said screw head, said screw body having a reduced diameter from said distal end to a diametrally enlarged shoulder adjacent said screw head, said reduced diameter passing through said transverse throughbore in said C-clamp in a nonbinding relationship, said screw body having a first set of threads with said diametrally enlarged shoulder having a second set of threads, said second set of threads being configured to threadedly engage said threads in said lower jaw of said C-clamp.

2. The spinal fixation apparatus defined in claim 1 wherein said bone screw includes said first set of threads and said second set of threads having an identical thread pitch.

3. The spinal fixation apparatus defined in claim 2 wherein said threads have an angled face toward said distal end and an orthogonally oriented face toward said proximal end.

4. The spinal fixation apparatus defined in claim 1 wherein said spinal fixation apparatus includes a second longitudinal rod spaced from said longitudinal rod and with a second plurality of said stem clamps mounted to said second longitudinal rod, a second plurality of said C-clamps mounted to said stems of said second plurality of said stem clamps, and a second plurality of said bone screws mounting said C-clamps to the bone.

5. The spinal fixation apparatus defined in claim 4 wherein said spinal fixation apparatus includes a cross-link plate mounted between said longitudinal rod and said second longitudinal rod, said cross-link plate having a first end and a second end with a first eyelet formed in said first end and a second eyelet formed in said second end, said cross-link plate having a shank extending between said first eyelet and said second eyelet, said shank having a square profile at the midsection of said shank.

6. The spinal fixation apparatus defined in claim 1 wherein said C-clamp includes an angular offset of said lower jaw from said upper jaw, said angular offset having an angle within the range on the order of about one degree to ten degrees.

7. The spinal fixation apparatus defined in claim 1 wherein said C-clamp includes a detent means as an engagement means on said C-clamp.

8. The spinal fixation apparatus defined in claim 1 wherein said stem clamp includes an angular offset of said lower jaw from said upper jaw, said angular offset having an angle within the range on the order of about one degree to ten degrees.

9. The spinal fixation apparatus defined in claim 1 wherein said longitudinal rod includes a right angle bend formed in said longitudinal rod.

10. The spinal fixation apparatus defined in claim 1 wherein said stem on said stem clamp is of the same diameter as said longitudinal rod.

11. The spinal fixation apparatus defined in claim 1 wherein said C-clamp includes a bone pin for temporarily mounting said spinal fixation apparatus to the spine prior to inserting said bone screws into the spine.

12. The spinal fixation apparatus defined in claim 11 wherein said bone pin comprises a handle segment for hand grasping said bone pin and a pin segment for insertion through said C-clamp and into the bone of the spine, said bone pin thereby releasably mounting said C-clamp to the spine.

13. A spinal fixation apparatus for implantation on a spine comprising:

a first longitudinal rod for placement on the spine at one side of and generally parallel to the spinous process of the spine;

a second longitudinal rod for placement on the spine at the other side of and generally parallel to the spinous process of the spine;

a plurality of stem clamps mounted to said first longitudinal rod and said second longitudinal rod;

a plurality of C-clamps mounted to said stem clamps and to said first longitudinal rod and to said second longitudinal rod, said C-clamp comprising a clamp body having an upper law and a lower jaw with a lateral throughbore passing between said upper jaw and said lower jaw, said clamp body having a transverse throughbore passing orthogonally through said upper jaw and said lower jaw with the portion of said transverse throughbore in said lower jaw having threads therein, said C-clamp further including engagement means for engaging said C-clamp with said bone screw, said bone screw comprising a bolt head at a proximal end and a tip at a distal end, said bone screw having a threaded shaft between said proximal end and said distal end with said threaded shaft having a threaded, diametrally enlarged shoulder adjacent said bolt head and a threaded, diametrally reduced screw body between said shoulder and said tip, the thread pitch for said threaded, diametrally enlarged shoulder being identical to said threaded, diametrally reduced screw body, said threaded, diametrally enlarged shoulder threadedly engaging said threads in said transverse throughbore in said lower jaw of said C-clamp thereby providing said engagement means for said C-clamp;

a plurality of bone screws mounted to said C-clamps, said bone screws being operable to secure said C-clamps to the spine; and at least one cross-link plate interconnecting said first longitudinal rod to said second longitudinal rod.

14. The spinal fixation apparatus defined in claim 13 wherein each of said first longitudinal rod and said second longitudinal rod includes a right angle bend.

15. The spinal fixation apparatus defined in claim 13 wherein said stem clamp comprises a clamp body having an upper jaw and a lower jaw with a lateral throughbore passing between one edge of said clamp body, said throughbore telescopically selectively receiving said first and second longitudinal rods, said clamp body including a transverse throughbore passing orthogonally through said upper jaw and said lower jaw with the portion of said transverse throughbore through said lower jaw having threads therein, said clamp body including a stem extending orthogonally therefrom, said stem clamp including a bolt means for threadedly engaging said threads to bring said upper jaw toward said lower jaw and constrict said lateral throughbore thereby securing said stem clamp to said longitudinal rod.

16. The spinal fixation apparatus defined in claim 13 wherein said upper jaw includes an angular offset from said lower jaw to accommodate being compressed downwardly upon tightening with said bone screw, said angular offset comprising an angle within the range on the order of about one degree to ten degrees.

17. The spinal fixation apparatus defined in claim 13 wherein said stem clamp includes a lower jaw and an upper jaw, said lower jaw having an angular offset from said upper jaw, said angular offset being within the range on the order of about one to ten degrees.

18. The spinal fixation apparatus defined in claim 13 wherein said bone screw comprises a screw having a head at a proximal end and a tip at a distal end, said screw having a diametrally enlarged shoulder adjacent said head, said shoulder having a first set of threads, said screw including a shaft extending between said shoulder and said tip, said shaft being diametrally smaller than said shoulder and having a second set of threads, said second set of threads having the same thread pitch as said first set of threads.

19. The spinal fixation apparatus defined in claim 18 wherein said second set of threads includes a thread profile having a planar face orthogonal to the axis of said shaft, said planar face being oriented toward said head.

20. The spinal fixation apparatus defined in claim 13 wherein said C-clamp includes a bone pin for temporarily mounting said C-clamp to the spine prior to inserting said bone screw, said bone pin having a handle and a pin extending therefrom, said pin having a reduced diameter to pass through said C-clamp and into the bone.

21. A method for providing fixation of a spine comprising the steps of:

obtaining a longitudinal rod;

preparing a plurality of stem clamps with stems extending therefrom;

mounting said stem clamps to said longitudinal rod;

fabricating a plurality of C-clamps;

affixing said C-clamps to said longitudinal rod and to said stems of said stem clamps;

forming a plurality of bone screws;

securing said C-clamps to a spine with said bone screws; and tightening said stem clamps and said C-clamps thereby providing spinal fixation with said longitudinal rod.

22. A method for providing fixation of a spine comprising the steps of:

obtaining a longitudinal rod;

preparing a plurality of stem clamps with stems extending therefrom;

mounting said stem clamps to said longitudinal rod;

fabricating a plurality of C-clamps, said fabricating step including forming said plurality of bone screws with a first threaded section and a second threaded section, said first threaded section having a smaller diameter sufficient to pass through said transverse throughbore in said C-clamp, said second threaded section threadedly engaging said set of threads in said C-clamp thereby selectively clamping said C-clamp to said longitudinal rod and said stem;

affixing said C-clamps to said longitudinal rod and to said stems of said stem clamps;

forming a plurality of bone screws;

securing said C-clamps to a spine with said bone screws; and tightening said stem clamps and said C-clamps thereby providing spinal fixation with said longitudinal rod.

23. The method defined in claim 22 wherein said fabricating step includes preparing said C-clamp as a pair of opposed jaws having a lateral throughbore therethrough for slideably receiving said longitudinal rod or said stem of said stem clamp, said preparing step including forming a transverse throughbore through said upper jaw and said lower jaw and creating a set of threads in the lower jaw portion of said transverse throughbore.

24. The method defined in claim 22 wherein said obtaining step includes providing a second longitudinal rod and affixing said second longitudinal rod to the spine along with said longitudinal rod using said stem clamps, said C-clamps, and said bone screws.

25. The method defined in claim 24 wherein said providing step includes coupling said longitudinal rod to said second longitudinal rod with a cross-link plate.

26. The method defined in claim 25 wherein said coupling step includes forming said cross-link plate with a first end and a second end and a first eyelet in said first end and a second eyelet at said second end, said forming step including providing a shank between said first eyelet and said second eyelet, said providing step including forming said shank with a square cross-sectional profile thereby deformably adjusting said cross-link plate to said longitudinal rod and said second longitudinal rod.

27. The method defined in claim 22 wherein said forming step includes preparing threads on said bone screw for securely engaging bone with said threads, said preparing step including shaping said threads with a generally flat surface orthogonal to the axis of said bone screw, said flat surface being oriented to the outer surface of the bone as said bone screw is inserted into the bone.

28. The method defined in claim 22 wherein said affixing step includes obtaining a plurality of bone pins and ascertaining the placement of said longitudinal rod, said stem clamps, and said C-clamps prior to said securing step by mounting said C-clamps to the spine with said bone pins.

*29. A spinal fixation apparatus comprising:*

*a first elongate support member having a right-angle bend formed therein such that said support member assumes an "L" shape having a first, longer portion and a second, shorter portion extending at a substantially right angle with respect to said longer portion; and*

*attaching means for releasably attaching the first elongate support member to at least two vertebrae of a human spine to thereby intercouple said vertebrae to one another.*

*30. The spinal fixation apparatus of claim 29, wherein the attaching means further comprises means for intercoupling the first elongate support member to at least three different vertebrae of the spine.*

*31. The spinal fixation apparatus defined in claim 29, wherein the first, longer portion is at least three times the length of the second, shorter portion.*

*32. The spinal fixation apparatus defined in claim 29, wherein the apparatus further comprises a second elongate support member with a means for attaching in a substantially parallel fashion the second elongate support member parallel to and apart from the first elongate support member on the spine, said second elongate support member having a right-angle bend formed therein such that said second elongate support member assumes an "L" shape having a first, longer portion and a second, shorter portion extending at a substantially right angle with respect to said longer portion.*

*33. The spinal fixation apparatus defined in claim 32, wherein the apparatus further comprises a means for intercoupling the first elongate support member with the second elongate support member, such that the longer portion of said first elongate support member is spaced apart from the longer portion of said second elongate support member.*

*34. The spinal fixation apparatus defined in claim 33, wherein the means for attaching in a substantially parallel fashion comprises at least one stem clamp that is releasably mountable to the corresponding first elongate support member or the second elongate support member, the stem clamp comprising a concave sidewall, a body and a stem, said concave sidewall having a limited degree of resiliency and defining a lateral throughbore for holding the first elongate support member and the second elongate support member in place, said concave sidewall interconnecting with said body, said body comprising an upper jaw and a lower jaw, said upper jaw having a transverse, non-threaded throughbore formed therein, said lower jaw having a transverse, threaded throughbore formed therein such that a fastener may pass through the upper jaw unobstructed while threadedly engaging the lower jaw such that threaded engagement operates to compress the concave sidewall, said upper jaw being attached to the stem.*

*35. The spinal fixation apparatus defined in claim 34, wherein the means for intercoupling the first elongate support member with the second elongate support member comprises the stem clamp and a cross-link member, wherein the cross-link member extends between the first elongate support member and the second elongate support member interconnecting said first elongate support member and said second elongate support member providing additional stabilization of the apparatus.*

*36. The spinal fixation apparatus defined in claim 35, wherein the cross-link member is fastened to the stem clamp by the fastener of the stem clamp, at least one of said stem clamp corresponding to the first elongate support member and the second elongate support member, wherein a first eyelet and a second eyelet of said cross-link member are aligned along the top of the transverse throughbore of the upper jaw of the stem clamp such that the fastener may pass therethrough thereby causing attachment of said cross-link member to said stem clamp interconnecting the first elongate support member and the second elongate support member for increased stabilization.*

*37. The spinal fixation apparatus defined in claim 34, wherein the stem of the stem clamp is attached to the body of said stem clamp independently of the fastener.*

*38. The spinal fixation apparatus defined in claim 34, wherein the stem clamp is configured and arranged to permit the first elongate support member to pass through space surrounded by the concave sidewall such that the concave sidewall compressibly grips upon the first elongate support member.*

*39. The spinal fixation apparatus defined in claim 34, wherein the lateral throughbore of the stem clamp has an interior diameter that is greater than the diameter of the first elongate support member when said stem clamp resides in a natural unbiased state to thereby allow said first elongate support member to slide through the lateral throughbore*

*prior to the fastener engaging the threaded lower jaw compressing the concave sidewall and gripping the first elongate support member.*

*40. The spinal fixation apparatus defined in claim 34, wherein the stem of the stem clamp extends laterally from the upper jaw of the body of the stem clamp.*

*41. The spinal fixation apparatus defined in claim 34, wherein the stem clamp having an angular offset of said lower jaw from said upper jaw, said angular offset having an angle between the range of approximately one to ten degrees.*

*42. The spinal fixation apparatus defined in claim 29, wherein the attaching means further comprises at least one C-clamp having a clamp body, the clamp body having an upper jaw and a lower jaw with a lateral throughbore passing between said upper jaw and said lower jaw.*

*43. The spinal fixation apparatus defined in claim 42, wherein the clamp body further having a transverse throughbore passing through the upper jaw and the lower jaw with the transverse throughbore in said lower jaw having threads therein, said C-clamp further including engagement means for engaging said C-clamp with a bone screw, said bone screw comprising a bolt head at a proximal end and a tip at a distal end, said bone screw having a threaded shaft between said proximal end and said distal end with said threaded shaft having a threaded, diametrally enlarged shoulder adjacent said bolt head and a threaded, diametrally reduced screw body between said shoulder and said tip, the thread pitch for said threaded, diametrally enlarged shoulder being identical to said threaded, diametrally reduced screw body, said threaded, diametrally enlarged shoulder threadedly engaging said threads in said transverse throughbore in said lower jaw of said C-clamp thereby providing said engagement means for said C-clamp.*

*44. The spinal fixation apparatus defined in claim 29, wherein the apparatus further comprises:*

*a second elongate support member with a means for attaching in a substantially parallel fashion the second elongate support member parallel to and apart from the first elongate support member on the spine, said second elongate support member having a right-angle bend formed therein such that said second elongate support member assumes an "L" shape having a first, longer portion and a second, shorter portion extending at a substantially right angle with respect to said longer portion;*

*wherein the apparatus further comprises a means for intercoupling the first elongate support member with the second elongate support member, such that the longer portion of said first elongate support member is spaced apart from the longer portion of said second elongate support member;*

*wherein the means for attaching in a substantially parallel fashion comprises at least one stem clamp releasably mountable to the first elongate support member and the second elongate support member, the stem clamp comprising a concave sidewall, a body and a stem, said concave sidewall having a limited degree of resiliency and defining a lateral throughbore for holding the first elongate support member and the second elongate support member in place, said concave sidewall interconnecting with said body, said body comprising an upper jaw and a lower jaw, said upper jaw having a transverse, non-threaded throughbore formed therein, said lower jaw having a transverse, threaded throughbore formed therein such that a fastener may pass through the upper jaw unobstructed while threadedly engaging the lower jaw such that said threaded engagement operates to compress the concave sidewall, said upper jaw being attached to the stem;*

*wherein the means for intercoupling the first elongate support member with the second elongate support member comprises the stem clamp and a cross-link member, wherein the cross-link member extends between the first elongate support member and the second elongate support member interconnecting said first elongate support member and said second elongate support member providing additional stabilization of the apparatus;*

*wherein the stem of the stem clamp is attached to the body of said stem clamp independently of the fastener;*

*wherein the stem clamp is configured and arranged to permit the first elongate support member to pass through space surrounded by the concave sidewall such that the concave sidewall compressibly grips upon the first elongate support member;*

*wherein the lateral throughbore of the stem clamp has an interior diameter that is greater than the diameter of the first elongate support member when said stem clamp resides in a natural unbiased state to thereby allow said first elongate support member to slide through the lateral throughbore prior to the fastener engaging the threaded lower jaw compressing the concave sidewall and gripping the first elongate support member;*

*wherein the stem of the stem clamp extends laterally from the upper jaw of the body of the stem clamp;*

*wherein the stem clamp having an angular offset of said lower jaw from said upper jaw, said angular offset having an angle between the range of approximately one to ten degrees.*

*45. A spinal fixation apparatus for implantation on a spine comprising:*

*a first longitudinal rod comprising a first end and a second end, the first longitudinal rod further comprises at least one bend located between the first end and the second end of said first longitudinal rod forming a side arm; and*

*at least one stem clamp releasably mountable to said first longitudinal rod, the stem clamp comprising a concave sidewall, a body and a stem, the concave sidewall having a limited degree of resiliency and defining a lateral throughbore for holding the first longitudinal rod in place, said concave sidewall interconnecting with the body, said body comprising an upper jaw and a lower jaw, the upper jaw having a transverse, non-threaded throughbore formed therein, the lower jaw having a transverse, threaded throughbore formed therein such that a fastener may pass through said upper jaw unobstructed while threadedly engaging said lower jaw such that threaded engagement operates to compress said concave sidewall, said upper jaw being attached to the stem.*

*46. The spinal fixation apparatus defined in claim 45, wherein the stem of the stem clamp is attached to the body of said stem clamp independently of the fastener.*

*47. The spinal fixation apparatus defined in claim 45, wherein the stem clamp is configured and arranged to permit the first longitudinal rod to pass through space surrounded by the concave sidewall such that said concave sidewall compressibly grips upon said first longitudinal rod.*

*48. The spinal fixation apparatus defined in claim 45, wherein the lateral throughbore of the stem clamp has an*

*interior diameter that is greater than the diameter of the first longitudinal rod when said stem clamp resides in a natural unbiased state to thereby allow said first longitudinal rod to slide through said lateral throughbore of said stem clamp prior to the compression of the concave sidewall bringing the lower jaw into contact with the upper jaw and gripping said first longitudinal rod.*

*49. The spinal fixation apparatus defined in claim 45, wherein the stem of the stem clamp extends laterally from the upper jaw of the body of said stem clamp.*

*50. The spinal fixation apparatus defined in claim 45, wherein the stem clamp having an angular offset of the lower jaw from the upper jaw, said angular offset having an angle between the range of approximately one to ten degrees.*

*51. The spinal fixation apparatus defined in claim 45, wherein at least one C-clamp is releasably mountable to at least one of the group consisting of the stem of the stem clamp and the first longitudinal rod, said C-clamp comprising a clamp body having an upper jaw and a lower jaw with a lateral throughbore passing between said upper jaw and said lower jaw, said clamp body having a transverse throughbore passing through said upper jaw and said lower jaw with the transverse throughbore in said lower jaw having threads therein, said C-clamp further including engagement means for engaging said C-clamp with a bone screw, said bone screw comprising a bolt head at a proximal end and a tip at a distal end, said bone screw having a threaded shaft between said proximal end and said distal end with said threaded shaft having a threaded, diametrally enlarged shoulder adjacent said bolt head and a threaded, diametrally reduced screw body between said shoulder and said tip, the thread pitch for said threaded, diametrally enlarged shoulder being identical to said threaded, diametrally reduced screw body, said threaded, diametrally enlarged shoulder threadedly engaging said threads in said transverse throughbore in said lower jaw of said C-clamp thereby providing said engagement means for said C-clamp.*

*52. The spinal fixation apparatus defined in claim 45, wherein the first longitudinal rod having a right-angle bend formed therein such that said first longitudinal rod assumes an "L" shape having a first, longer portion and a second, shorter portion extending at a substantially right angle with respect to said longer portion.*

*53. The spinal fixation apparatus defined in claim 52, wherein the first, longer portion is at least three times the length of the second, shorter portion.*

*54. The spinal fixation apparatus defined in claim 45, wherein the first longitudinal rod and the stem of the stem clamp have the same diameter.*

*55. The spinal fixation apparatus defined in claim 45, wherein the apparatus further comprises a second longitudinal rod placed parallel to and apart from the first longitudinal rod, the second longitudinal rod having a first end and a second end, said second longitudinal rod further having at least one bend located between the first end and the second end of said second longitudinal rod forming a side arm.*

*56. The spinal fixation apparatus defined in claim 55, wherein the second longitudinal rod being releasably mountable to the spine with at least one C-clamp, and selectively interconnected to the stem clamp, said stem clamp providing an additional attachment site closer to the pedicle of the spine for the C-clamp to interconnect with thereby providing additional stabilization of the apparatus on the spine.*

*57. The spinal fixation apparatus defined in claim 55, wherein the apparatus further comprises a cross-link member wherein the cross-link member extends between the first longitudinal rod and the second longitudinal rod interconnecting said first longitudinal rod and said second longitudinal rod providing additional stabilization of the apparatus.*

*58. The spinal fixation apparatus defined in claim 57, wherein the cross-link member is fastened to said stem clamp by the fastener of the stem clamp, at least one of said stem clamp corresponding to the first longitudinal rod and the second longitudinal rod, wherein a first eyelet and a second eyelet of said cross-link member are aligned along the top of the transverse throughbore of the upper jaw of the stem clamp such that the fastener may pass therethrough thereby causing attachment of said cross-link member to said stem clamp interconnecting the first longitudinal rod and the second longitudinal rod for increased stabilization.*

*59. The spinal fixation apparatus defined in claim 45, wherein:*

*the stem clamp is configured and arranged to permit the first longitudinal rod to pass through space surrounded by the concave sidewall such that the concave sidewall compressibly grips upon the first longitudinal rod;*

*the stem of the stem clamp is attached to the body of said stem clamp independently of the fastener, wherein said stem of said stem clamp extends laterally from the upper jaw of the body of the stem clamp;*

*the lateral throughbore of the stem clamp has an interior diameter that is greater than the diameter of the first longitudinal rod when said stem clamp resides in a natural unbiased state to thereby allow said first longitudinal rod to slide through the lateral throughbore prior to the fastener engaging the threaded lower jaw compressing the concave sidewall and gripping the first longitudinal rod;*

*the stem clamp having an angular offset of the lower jaw from the upper jaw, said angular offset having an angle between the range of approximately one to ten degrees.*

*60. The spinal fixation apparatus defined in claim 45, wherein the apparatus further comprises:*

*a second longitudinal rod having a right-angle bend formed therein such that said second longitudinal rod assumes an "L" shape having a first, longer portion and a second, shorter portion extending at a substantially right angle with respect to said longer portion, said first, longer portion is about three times the length of said second, shorter portion; and*

*wherein a right-angle bend formed in the first longitudinal rod such that said first longitudinal rod assumes an "L" shape having a first, longer portion and a second, shorter portion extending at a substantially right angle with respect to said longer portion, said first, longer portion is about three times the length of said second, shorter portion;*

*a cross-link member wherein the cross-link member extends between the first longitudinal rod and the second longitudinal rod interconnecting said first longitudinal rod and said second longitudinal rod providing additional stabilization of the apparatus;*

*wherein the cross-link member intercouples the first longitudinal rod with the second longitudinal rod, such that the longer portion of said first longitudinal rod is spaced apart from the longer portion of said second longitudinal rod;*

*wherein at least one stem clamp releasably mountable to the first longitudinal rod and the second longitudinal rod for attaching in a substantially parallel fashion;*

*wherein the stem of the stem clamp is attached to the body of said stem clamp independently of the fastener;*

*wherein the stem clamp is configured and arranged to permit the first longitudinal rod to pass through space surrounded by the concave sidewall such that the concave sidewall compressibly grips upon said first longitudinal rod;*

*wherein the lateral throughbore of the stem clamp has an interior diameter that is greater than the diameter of the first longitudinal rod when said stem clamp resides in a natural unbiased state to thereby allow said first longitudinal rod to slide through the lateral throughbore prior to the fastener engaging the threaded lower jaw compressing the concave sidewall and gripping the first longitudinal rod;*

*wherein the stem of the stem clamp extends laterally from the upper jaw of the body of the stem clamp;*

*wherein the stem clamp having an angular offset of said lower jaw from said upper jaw, said angular offset having an angle between the range of approximately one to ten degrees;*

*wherein the first longitudinal rod and the stem of the stem clamp have the same diameter.*

*61. A spinal fixation apparatus comprising:*

*a first elongate support member having a right-angle bend formed therein such that said support member assumes an "L" shape having a first, longer portion and a second, shorter portion extending at a substantially right angle with respect to said longer portion; and*

*attaching means for releasably attaching the first elongate support member to at least two vertebrae of a human spine to thereby intercouple said vertebrae to one another;*

*wherein the attaching means further comprises means for intercoupling the first elongate support member to at least three different vertebrae of the spine;*

*wherein the first, longer portion is at least three times the length of the second, shorter portion;*

*wherein the apparatus further comprises a second elongate support member with a means for attaching in a substantially parallel fashion the second elongate support member parallel to and apart from the first elongate support member on the spine, said second elongate support member having a right-angle bend formed therein such that said second elongate support member assumes an "L" shape having a first, longer portion and a second, shorter portion extending at a substantially right angle with respect to said longer portion;*

*wherein the apparatus further comprises a means for intercoupling the first elongate support member with the second elongate support member, such that the longer portion of said first elongate support member is spaced apart from the longer portion of said second elongate support member;*

*wherein the means for attaching in a substantially parallel fashion comprises at least one stem clamp that is releasably mountable to the corresponding first elongate support member or the second elongate support member, the stem clamp comprising a concave sidewall, a body and a stem, said concave sidewall having a limited degree of resiliency and defining a lateral throughbore for holding the first elongate support member and the second elongate support member in place, said concave sidewall interconnecting with said body, said body comprising an upper jaw and a lower jaw, said upper jaw having a transverse, non-threaded throughbore formed therein, said lower jaw having a transverse, threaded throughbore formed therein such that a fastener may pass through the upper jaw unobstructed while threadedly engaging the lower jaw such that said threaded engagement operates to compress the concave sidewall, said upper jaw being attached to the stem;*

*wherein the means for intercoupling the first elongate support member with the second elongate support member comprises the stem clamp and a cross-link member, wherein the cross-link member extends between the first elongate support member and the second elongate support member interconnecting said first elongate support member and said second elongate support member providing additional stabilization of the apparatus;*

*wherein the cross-link member is fastened to the stem clamp by the fastener of the stem clamp, at least one of said stem clamp corresponding to the first elongate support member and the second elongate support member, wherein said first eyelet and said second eyelet of said cross-link member are aligned along the top of the transverse throughbore of the upper jaw of the stem clamp such that the fastener may pass therethrough thereby causing attachment of said cross-link member to said stem clamp interconnecting the first elongate support member and the second elongate support member for increased stabilization;*

*wherein the stem of the stem clamp is attached to the body of said stem clamp independently of the fastener;*

*wherein the stem clamp is configured and arranged to permit the first elongate support member to pass through space surrounded by the concave sidewall such that the concave sidewall compressibly grips upon the first elongate support member;*

*wherein the lateral throughbore of the stem clamp has an interior diameter that is greater than the diameter of the first elongate support member when said stem clamp resides in a natural unbiased state to thereby allow said first elongate support member to slide through the lateral throughbore prior to the fastener engaging the threaded lower jaw compressing the concave sidewall and gripping the first elongate support member;*

*wherein the stem of the stem clamp extends laterally from the upper jaw of the body of the stem clamp; and*

*wherein the stem clamp having an angular offset of said lower jaw from said upper jaw, said angular offset having an angle between the range of approximately one to ten degrees.*

*62. A spinal fixation apparatus for implantation on a spine comprising:*

*at least one longitudinal rod comprising a first end and a second end, said longitudinal rod further comprises at least one bend located between the first end and the second end of said longitudinal rod forming a side arm;*

*at least one stem clamp releasably mountable to said longitudinal rod, said stem clamp comprising a concave sidewall, a body and a stem, said concave sidewall having a limited degree of resiliency and defining a lateral throughbore for holding the longitudinal rod in place, said concave sidewall interconnecting with said body, said body comprising an upper jaw and a lower jaw, said upper jaw having a transverse, non-*

*threaded throughbore formed therein, said lower jaw having a transverse, threaded throughbore formed therein such that a fastener may pass through the upper jaw unobstructed while threadedly engaging the lower jaw such that threaded engagement operates to compress the concave sidewall, said upper jaw being attached to the stem; and*

*at least one C-clamp mounted to at least one of the group consisting of the stem of the stem clamp and the longitudinal rod, said C-clamp comprising a clamp body having an upper jaw and a lower jaw with a lateral throughbore passing between said upper jaw and said lower jaw, said clamp body having a transverse throughbore passing through said upper jaw and said lower jaw with the transverse throughbore in said lower jaw having threads therein, said C-clamp further including engagement means for engaging said C-clamp with a bone screw, said bone screw comprising a bolt head at a proximal end and a tip at a distal end, said bone screw having a threaded shaft between said proximal end and said distal end with said threaded shaft having a threaded, diametrally enlarged shoulder adjacent said bolt head and a threaded, diametrally reduced screw body between said shoulder and said tip, the thread pitch for said threaded, diametrally enlarged shoulder being identical to said threaded, diametrally reduced screw body, said threaded, diametrally enlarged shoulder threadedly engaging said threads in said transverse throughbore in said lower jaw of said C-clamp thereby providing said engagement means for said C-clamp.*

*63. A spinal fixation apparatus for implantation on a spine comprising:*

*at least one longitudinal rod comprising a first end and a second end, said longitudinal rod further comprises at least one bend located between the first end and the second end of said first longitudinal rod forming a side arm; and*

*at least one C-clamp mounted to said longitudinal rod, said C-clamp comprising a clamp body having an upper jaw and a lower jaw with a lateral throughbore passing between said upper jaw and said lower jaw, said clamp body having a transverse throughbore passing through said upper jaw and said lower jaw, said transverse throughbore in said lower jaw having threads therein.*

*64. A spinal fixation apparatus for implantation on a spine comprising:*

*at least one longitudinal rod comprising a first end and a second end, said longitudinal rod further comprises at least one bend located between the first end and the second end of said first longitudinal rod forming a side arm; and*

*at least one C-clamp mounted to said longitudinal rod, said C-clamp comprising a clamp body having an upper jaw and a lower jaw with a lateral throughbore passing between said upper jaw and said lower jaw, said clamp body having a transverse throughbore passing through said upper jaw and said lower jaw, said transverse throughbore in said lower jaw having threads therein; and*

*a bone screw comprising a bolt head at a proximal end and a tip at a distal end, said bone screw having a threaded shaft between said proximal end and said distal end with said threaded shaft having a threaded, diametrally enlarged shoulder adjacent said bolt head and a threaded, diametrally reduced screw body between said shoulder and said tip, the thread pitch for said threaded, diametrally enlarged shoulder being identical to said threaded, diametrally reduced screw body, said threaded, diametrally enlarged shoulder threadedly engaging said threads in said transverse throughbore in said lower jaw of said C-clamp thereby providing said engagement means for said C-clamp;*

*wherein the C-clamp further including engagement means for engaging said C-clamp with a bone screw.*

*65. A spinal fixation apparatus for implantation on a spine comprising:*

*a longitudinal rod comprising a first end and a second end, said longitudinal rod comprising at least one bend located between the first end and second end of said longitudinal rod forming a side arm;*

*a stem clamp having a concave sidewall, a body and a stem, said concave sidewall having a limited degree of resiliency for holding the longitudinal rod in place, said concave sidewall interconnecting with said body defining a lateral throughbore for engaging said longitudinal rod, said body comprising an upper jaw and a lower jaw, said upper jaw having a transverse throughbore formed therein, said lower jaw having a transverse throughbore formed therein, wherein a fastener may pass through the upper jaw while engaging the lower jaw such that the fastener urges the upper jaw and the lower jaw together through compression forces to thereby fasten the stem clamp to the longitudinal rod; and*

*attaching means for attaching said stem of said stem clamp and said longitudinal rod to the spine thereby immobilizing at least two vertebrae of the spine increasing the rigidity of the spine for the stabilization and subsequent fusion of the vertebrae.*

*66. A spinal fixation apparatus comprising:*

*an elongate support member having a right-angle bend formed therein such that said support member assumes an "L" shape having a first, longer portion and a second, shorter portion extending at a substantially right angle with respect to said longer portion;*

*attaching means for releasably attaching the elongate support member to at least two vertebrae of a human spine to thereby intercouple said vertebrae to one another; and*

*a second elongate support member with a means for attaching in a substantially parallel fashion the second elongate support member parallel to and apart from the first elongate support member on the spine, said second elongate support member having a right-angle bend formed therein such that said second elongate support member assumes an "L" shape having a first, longer portion and a second, shorter portion extending at a substantially right angle with respect to said longer portion;*

*wherein the apparatus further comprises a means for intercoupling the first elongate support member with the second elongate support member, such that the longer portion of said first elongate support member is spaced apart from the longer portion of said second elongate support member;*

*wherein the attaching means further comprises means for intercoupling the elongate support member to at least three different vertebrae of the spine;*

*wherein the attaching means further comprises at least one C-clamp having a clamp body, the clamp body*

*having an upper jaw and a lower jaw with a lateral throughbore passing between said upper jaw and said lower jaw;*

*wherein the clamp body of the C-clamp further having a transverse throughbore passing through the upper jaw and the lower jaw with the transverse throughbore in said lower jaw having threads therein, said C-clamp further including engagement means for engaging said C-clamp with a bone screw, said bone screw comprising a bolt head at a proximal end and a tip at a distal end, said bone screw having a threaded shaft between said proximal end and said distal end with said threaded shaft having a threaded, diametrally enlarged shoulder adjacent said bolt head and a threaded, diametrally reduced screw body between said shoulder and said tip, the thread pitch for said threaded, diametrally enlarged shoulder being identical to said threaded, diametrally reduced screw body, said threaded, diametrally enlarged shoulder threadedly engaging said threads in said transverse throughbore in said lower jaw of said C-clamp thereby providing said engagement means for said C-clamp;*

*wherein the C-clamp is releasably mountable to the second, shorter portion of the elongate support member to thereby anchor the elongate support member to the spine;*

*wherein the C-clamp having an angular offset of said lower jaw from said upper jaw, said angular offset having an angle between the range of approximately one to ten degrees; and*

*wherein the first, longer portion is at least three times the length of the second, shorter portion.*

*67. A method for providing fixation of a spine comprising:*

*(a) selecting an elongate support member having a right-angle bend formed therein such that said support member assumes an "L" shape having a first, longer portion and a second, shorter portion extending at a substantially right angle with respect to said longer portion; and*

*(b) releasably attaching the elongate support member to at least two vertebrae of a human spine to thereby intercouple said vertebrae to one another, and releasably attaching at least three stem clamps to the longer portion of the elongate support member, and attaching each of said stem clamps to a bone screw.*

*68. A method for providing fixation of a spine comprising the steps of:*

*obtaining at least one longitudinal rod having a right-angle bend formed therein such that said support member assumes an "L" shape having a first, longer portion and a second, shorter portion extending at a substantially right angle with respect to said longer portion;*

*providing at least one C-clamp having an upper jaw, a lower jaw, and a lateral throughbore, the lower jaw having a threaded transverse throughbore;*

*affixing said C-clamp to said longitudinal rod such that the longitudinal rod is located within the lateral throughbore;*

*providing at least one bone screw having a head and a shaft with a threaded shoulder disposed between the head and the shaft for matingly engaging the threaded transverse throughbore of the lower jaw;*

*securing said C-clamp to a spine with said bone screw; and*

*tightening said bone screw such that the head contacts the upper jaw causing the upper jaw to move to a position closer in proximity with respect to the lower jaw, such that the C-clamp provides spinal fixation with said longitudinal rod.*

*69. A method for providing fixation of a spine comprising the steps of:*

*obtaining at least one longitudinal rod having a right-angle bend formed therein such that said support member assumes an "L" shape having a first, longer portion and a second, shorter portion extending at a substantially right angle with respect to said longer portion;*

*fabricating at least one stem clamp;*

*affixing said stem clamp to said longitudinal rod;*

*forming at least one bone screw;*

*securing said stem clamp to a spine with said bone screw; and*

*tightening said stem clamp thereby providing spinal fixation with said longitudinal rod.*

*70. A spinal fixation apparatus comprising:*

*a first elongate support having a right-angle bend formed therein such that said support member has a first portion and a second portion, said second portion extending at a substantially right angle with respect to said first portion; and*

*attaching means for releasably attaching the first elongate support member to at least two vertebrae of a human spine to thereby intercouple said vertebrae to one another.*

*71. The spinal fixation apparatus of claim 70, wherein the attaching means comprises a bone screw having a threaded shaft located between a proximal end and a distal end with the threaded shaft having a shoulder adjacent a head of the bone screw, wherein the shoulder is enlarged with respect to said threaded shaft.*

*72. The spinal fixation apparatus of claim 71, wherein the attaching means further comprises a C-clamp having an upper jaw, a lower jaw, and a lateral throughbore configured and dimensioned to receive the first elongate support member therein, wherein said C-clamp further comprises a transverse throughbore in the upper jaw and in the lower jaw, such that the enlarged shoulder of the bone screw engages the transverse throughbore of the lower jaw when the shaft of the bone screw is inserted through the transverse throughbore of the upper jaw and the transverse throughbore of the lower jaw.*

*73. A spinal fixation apparatus comprising:*

*a first elongate support member;*

*a clamping member comprising a clamp body, the clamp body having an upper jaw and a lower jaw, with a lateral throughbore defined by a sidewall passing between the upper jaw and the lower jaw, the lateral throughbore being configured and dimensioned to receive therein the first elongate support member; and*

*a slit comprising a first opening and a second opening, wherein the first opening is formed between the upper jaw and the lower jaw adjacent the lateral throughbore, and wherein the second opening is formed between the upper jaw and the lower jaw opposite the first opening;*

*wherein the second opening is larger than the first opening in an uncompressed, relaxed state, such that a lever is created to efficiently clamp the sidewall of the lateral throughbore against the first elongate support member as a compression force is applied to the clamping*

*member, when the first elongate support member is located within the lateral throughbore;*

*wherein the clamping member comprises a stem clamp having a stem extending from and being attached to the upper jaw.*

*74. A spinal fixation apparatus comprising:*

*a clamping member comprising a clamp body, the clamp body having an upper jaw and a lower jaw with a lateral throughbore defined by a sidewall passing between the upper jaw and the lower jaw, the lateral throughbore being configured and dimensioned to receive therein an elongate support member;*

*wherein the upper jaw of the clamping member comprises a top and bottom surface, and the lower jaw of the clamping member comprises a top and bottom surface;*

*wherein the top surface of the upper jaw is angularly offset from and with respect to the bottom surface of the lower jaw;*

*wherein the clamping member is a stem clamp, wherein the stem clamp further comprises a stem extending outwardly from the upper jaw.*

* * * * *